(12) United States Patent
Kabanov et al.

(10) Patent No.: US 7,169,411 B1
(45) Date of Patent: Jan. 30, 2007

(54) COMPOSITION FOR DELIVERY OF BIOLOGICAL AGENTS AND METHODS FOR THE PREPARATION THEREOF

(75) Inventors: Alexander V. Kabanov, Omaha, NE (US); Adi Eisenberg, Montreal (CA); Victor A. Kabanov, Moscow (RU)

(73) Assignees: The University of Nebraska Board of Regents, Lincoln, NE (US); McGill University, Montreal (CA); The Moscow State University, Moscow (RU)

( * ) Notice: Subject to any disclaimer, the term of this patent is extended or adjusted under 35 U.S.C. 154(b) by 0 days.

(21) Appl. No.: 09/445,653

(22) PCT Filed: Jun. 11, 1998

(86) PCT No.: PCT/US98/12138

§ 371 (c)(1),
(2), (4) Date: Jul. 17, 2000

(87) PCT Pub. No.: WO98/56348

PCT Pub. Date: Dec. 17, 1998

Related U.S. Application Data

(60) Provisional application No. 60/049,552, filed on Jun. 13, 1997.

(51) Int. Cl.
*A61K 9/10* (2006.01)
*A61K 47/30* (2006.01)

(52) U.S. Cl. ..................... 424/486; 424/487
(58) Field of Classification Search ............. 424/195.1, 424/78.1, 486, 487; 514/3, 772.3; 510/114; 528/354
See application file for complete search history.

(56) References Cited

U.S. PATENT DOCUMENTS 5,112,611 A * 5/1992 Ahmad et al. ........... 424/195.1
5,410,016 A * 4/1995 Hubbell et al. ............ 528/354
5,531,917 A * 7/1996 Nakayama et al. ......... 510/114

FOREIGN PATENT DOCUMENTS

JP 08 165491 6/1996
RU 1 172 237 A 5/1995

OTHER PUBLICATIONS

Polymeric Materials Science and Engineering, vol. 76, No. 76, No. 227, Apr. 13–17, 1997, p. 227.
Journal of Controlled Release, NL, Elsevier, vol. 39, No. 2, May 1, 1996.

* cited by examiner

*Primary Examiner*—Edward J. Webman
(74) *Attorney, Agent, or Firm*—Dann, Dorfman, Herell and Skillman, P.C.

(57) ABSTRACT

A composition for facilitating delivery of biological agents, comprising a therapeutic or diagnostic agent and a supramolecular complex, the latter comprising (i) a block copolymer, having at least one nonionic, water soluble segment and at least one polyionic segment, and (ii) at least one charged surfactant having hydrophobic groups. The charge of the surfactant is opposite to the charge of the polyionic segment of the block copolymer. The constituents of the supramolecular complex are bound by interaction between the opposite charges thereof and between surfactant hydrophobic groups. The therapeutic or diagnostic agent may be an ionic substance, in which case the ionic substance has a net charge opposite to that of the block copolymer, the net charge being no more than 10.

23 Claims, 3 Drawing Sheets

COMPOSITION FOR DELIVERY OF BIOLOGICAL AGENTS AND METHODS FOR THE PREPARATION THEREOF

This application, which is the U.S. national stage of PCT/US98/12138, filed Jun. 11, 1998, claims the benefit of U.S. Provisional Patent Application No. 60/049,552, filed Jun. 13, 1997.

Pursuant to 35 U.S.C. §202(c), it is hereby acknowledged that the U.S. Government has certain rights in the invention described herein, which was made in part with funds from the National Science Foundation.

FIELD OF THE INVENTION

The present invention relates to compositions for the delivery of biological agents, including, without limitation, therapeutic and diagnostic agents, and in particular to compositions comprising such agents and a complex formed of a block ionomer and an oppositely charge surfactant that exhibits combined properties of amphiphilic block copolymers and polyelectrolyte-surfactant complexes.

DESCRIPTION OF RELATED ART

Polyelectrolyte complexes from DNA and a block ionomer containing a nonionic water soluble segment, e.g., poly(ethylene oxide) (PEO), and a polycation segment have been recently proposed to facilitate delivery of macromolecules, e.g., nucleic acids, into living cells, as a means of implementing gene therapy. In these complexes, the charges of the DNA are neutralized by the polycation segments while the complex remains soluble due to the effect of the PEO segments. Such systems belong to a broader class of polyelectrolyte complexes formed by block ionomers. Published reports on complexes from PEO-b-poly (L-lysine) cation and PEO-b-poly($\alpha$-$\beta$-aspartate) anion, as well as PEO-b-polymethacrylate anion and poly(N-ethyl-4-vinylpyridinium) cation have suggested that they represent a new type of chemical entity, with combined properties of amphiphilic block copolymers and polyelectrolyte complexes. Such systems are reported to be stable and soluble in aqueous solution and can form a microphase from the neutralized polyion segments surrounded by a shell from PEO segments. In addition, these complexes appear to form micelle-like aggregates with a concentration dependence resembling those characterized by a critical micelle concentration (CMC). At the same time, these systems behave like regular polyelectrolyte complexes, in that they are salt-sensitive since they tend to dissociate as the salt concentration increases beyond a critical value. Furthermore, they have been shown to participate in substitution reactions involving neutralized polyion segments. These systems are produced as a result of a polyion coupling reaction after mixing polyelectrolyte components. The stability of such systems critically depends on the number of the salt bonds between interacting polyelectrolytes of opposite charge. It takes at least ten salt bonds to form a cooperative system (Papisov and Litmanovich, *Adv. Polym. Sci.*, 1988, 90: 139). Preferably, the number of salt bonds should be twenty or more. This means that the complexes do not form if the net charge of the molecules is less that the minimal number needed to form the required number of salt bonds, i.e., less than 10 to 20. If it is assumed that a minimal molecular mass of a charged unit in the molecule of a polyelectrolyte is about 70, then the molecular mass of the components in such system should be more than about 700, preferably more than about 1,400. In practice, however, many charged units have molecular masses of about 200 and more. Furthermore, many interacting molecules are weak bases or acids that at physiological pH are charged 20 to 30%. This shall put the minimal molecular mass of polyions in these systems at least 3 to 5 times higher, i.e., at least about 2,000 to 7,000. Normally, the molecular masses of polynucleotides used in such systems are 8,000 to 10,000 and more. These systems therefore have a fundamental limitation in that they cannot be formed with substances having less than about 10–20 charges and molecular masses less than about 2,000–7,000.

SUMMARY OF THE INVENTION

In accordance with the present invention, there is provided a composition of matter comprising a therapeutic or diagnostic agent and a supramolecular complex, said complex comprising as constituents (i) a block copolymer, having at least one nonionic, water soluble segment and at least one polyionic segment, and (ii) at least one charged surfactant having hydrophobic groups, the charge of said surfactant being opposite to the charge of the polyionic segment of said block copolymer the constituents of said complex being bound by interaction between said opposite charges and between surfactant hydrophobic groups, and with the proviso that when said therapeutic or diagnostic agent is an ionic substance having a net charge opposite to the charge of said block copolymer, the net charge of said therapeutic or diagnostic agent is no than 10.

In formulating the above-mentioned supramolecular complex, the polyionic segment of the block copolymer may be polyanionic, in which case the surfactant is a cationic surfactant, or polycationic, in which case the surfactant is an anionic surfactant. The ratio of the net charge of the surfactant to the net charge of the polyionic segment present in the block copolymer of the complex is between about 0.01 and about 100, more preferably, between about 0.1 and about 10.

The biological agent compositions of the present invention afford many advantages over the above-mentioned, previously reported block ionomer-polyelectrolyte complexes. For example, the compositions of this invention can be used to improve the therapeutic index with relatively low-molecular mass biological agents, and biological agents having less than 10 charges. Further, they can facilitate administration of biological agents by increasing their aqueous solubility. They also increase the stability and decrease side effects of the biological agents in the body. They further increase bioavailability of the biological agent incorporated therein, after administration to the body. In addition the compositions of the invention provide for site-specific drug delivery and release in sites with acidic pH, such as tumors, bacteria, stomach, muscle tissues, or sites with alkali pH such as the gastrointestinal tract. They further provide for compartment-specific delivery of both macromolecule and small molecule biological agents into cells by releasing the biological agent in early endosomes, and enhancing its transport in the cytoplasm and cellular compartments.

DETAILED DESCRIPTION OF THE INVENTION

Figure 1:
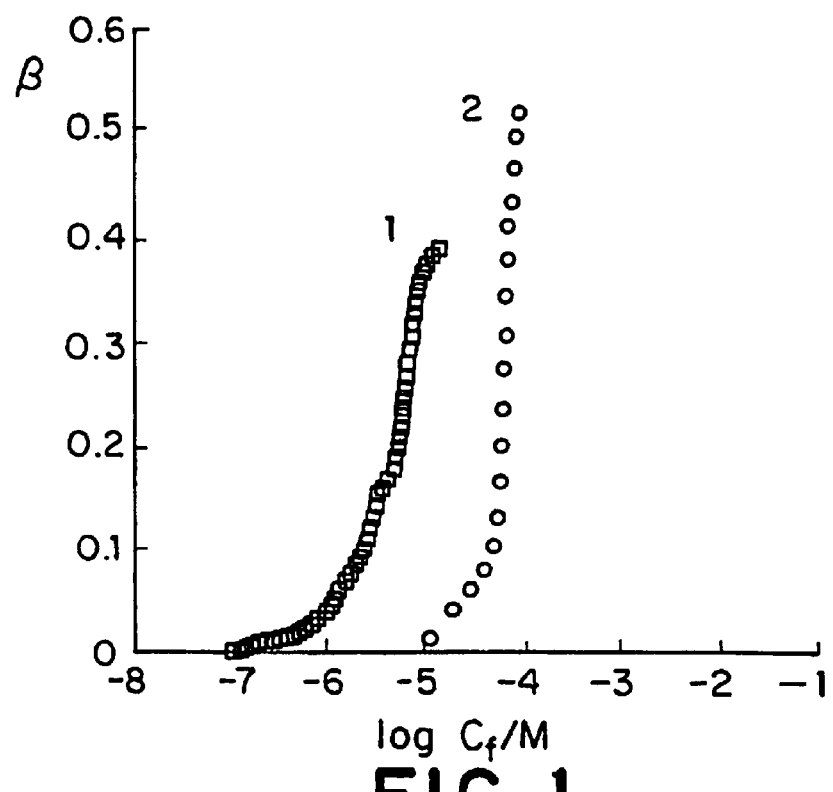
FIG. 1 is a graphical representation of binding isotherms of cetylpyridinium bromide (1) and dodecylpyridinium bromide (2) to polyethylene oxide-block-poly(sodium methacrylate), in which $\beta$, a fraction of occupied binding sites, is plotted as a function of surfactant concentration.

Filed concurrently with this application is an application Ser. No. 60/053,000 entitled "COMPOSITIONS FOR DELIVERY OF BIOLOGICAL AGENTS AND METHODS FOR THE PREPARATION THEREOF" with Alexander V. Kabanov, Adi Eisenberg and Victor A. Kabanov as the named inventors. The entire disclosure of Ser. No. 60/053,000 is hereby incorporated by reference herein.

The block copolymers used in the practice of this invention are most simply defined as conjugates of at least two different polymer segments (see, for example, Tirrel, *Interactions of Surfactants with Polymers and Proteins*. Goddard and Ananthapadmanabhan, Eds., pp. 59 et seq., CRC Press (1992)). Some block copolymer architectures are presented below:

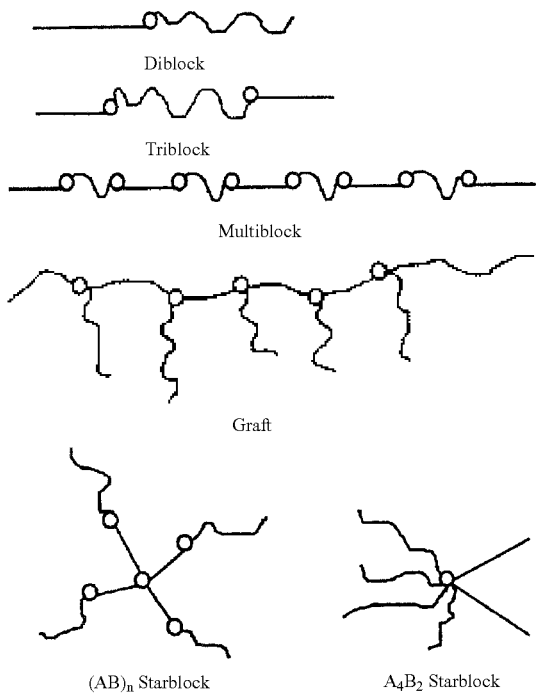

(AB)$_n$ Starblock    A$_4$B$_2$ Starblock

The simplest block copolymer architecture contains two segments joined at their termini to give an A-B type diblock. Consequent conjugation of more than two segments by their termini yields A-B-A type triblock, . . . ABAB . . . type multiblock, or even multisegment . . . ABC . . . architectures. If a main chain in the block copolymer can be defined in which one or several repeating units are linked to different polymer segments, then the copolymer have a graft architecture, e.g. A(B)$_n$ type. More complex architectures include for example (AB)$_n$ or A$_n$B$_m$ starblocks that have more than two polymer segments linked to a single center.

One method to produce block copolymers includes anionic polymerization with sequential addition of two monomers (see, for example, Schmolka, *J. Am. Oil Chem. Soc.* 1977, 54: 110; Wilczek-Vera et al., *Macromolecules* 1996, 29: 4036). This technique yields block copolymers with a narrow molecular mass distribution of the polymeric segments. Solid-phase synthesis of block copolymers has been developed recently that permit controlling the growth of the polymer segments with very high precision (Vinogradov et al., *Bioconjugate Chemistry* 1996, 7: 3). In some cases the block copolymers are synthesized by initiating polymerization of a polymer segment on ends of another polymer segment (Katayose and Kataoka, *Proc. Intern. Symp. Control. Rel. Bioact. Materials*, 1996, 23: 899) or by conjugation of complete polymer segments (Kabanov et al., *Bioconjugate Chem.* 1995, 6: 639; Wolfert et al., *Human Gene Ther.* 1996, 7: 2123). Properties of block copolymers in relation to this invention are determined by (1) block copolymer architecture and (2) properties of the polymer segments. They are independent of the chemical structure of the links used for conjugation of these segments (see, for example, Tirrel, supra; Sperling, *Introduction to Physical Polymer Science*, 2d edn., p. 46 et seq., John Wiley & Sons (1993)).

In one preferred embodiment the block copolymer is selected from the group consisting of polymers of formulas

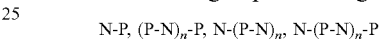

wherein N is a nonionic, water soluble segment ("N-type segment"), P is polyion segment ("P-type segment") and n is an integer from 1 to 5000. It is preferred that the degrees of polymerization of N-type and P-type segments are from about 3 to about 50000, more preferably from about 5 to about 5000, still more preferably from about 20 to about 500. If more than one segment of the same type comprise one block copolymer, then these segments may all have the same lengths or may have different lengths.

The preferred polyanion P-type segments include, but are not limited to those such as polymethacrylic acid and its salts, polyacrylic acid and its salts, copolymers of methacrylic acid and its salts, copolymers of acrylic acid and its salts, heparin, poly(phosphate), polyamino acid (e.g. polyaspartic acid, polyglutamic acid, and their copolymers containing a plurality of anionic units), polymalic acid, polylactic acid, polynucleotides, carboxylated dextran, and the like. Particularly preferred polyanion P-type segments are the products of polymerization or copolymerization of monomers that polymerize to yield a product having carboxyl pendant groups. Representative examples of such monomers are acrylic acid, aspartic acid 1,4-phenylenediacrylic acid, citraconic acid, citraconic anhydride, trans-cinnamic acid, 4-hydroxy-3-methoxy cinnamic acid, p-hydroxy cinnamic acid, trans-glutaconic acid, glutamic acid, itaconic acid, linoleic acid, linolenic acid, methacrylic acid, maleic acid, maleic anhydride, mesaconic acid, trans-β-hydromuconic acid, trans-trans muconic acid, oleic acid, ricinoleic acid, 2-propene-1-sulfonic acid, 4-styrene sulfonic acid, trans-traumatic acid, vinylsulfonic acid, vinyl phosphonic acid, vinyl benzoic acid and vinyl glycolic acid.

Preferred polycation P-type segments include but are not limited to polyamino acid (e.g., polylysine), alkanolamine esters of polymethacrylic acid (e.g., poly-(dimethylammonioethyl methacrylate), polyamines (e.g., spermine, polyspermine, polyethyleneimine), polyvinyl pyridine, and the quaternary ammonium salts of said polycation segments.

It is preferred to use nontoxic and non-immunogenic polymer-forming N-type and P-type segments. Because of elevated toxicity and immunogenicity of cationic peptides the non-peptide P-type segments are particularly preferred.

In the case of block copolymers having at least one polyanionic segment, the nonionic segment may include, without limitation, polyetherglycols (e.g. poly(ethylene oxide), poly(propylene oxide)) copolymers of ethylene oxide and propylene oxide, polysaccharides (e.g. dextran), products of polymerization of vinyl monomers (e.g., polyacrylamide, polyacrylic esters (e.g., polyacroloyl morpholine), polymethacrylamide, poly(N-(2-hydroxypropyl) methacrylamide, polyvinyl alcohol, polyvinyl pyrrolidone, polyvinyltriazole, N-oxide of polyvinylpyridine), polyortho esters, polyamino acids, polyglycerols (e.g., poly-2-methyl-oxazoline, poly-2-ethyl oxazoline) and copolymers and derivatives thereof.

Block copolymers comprising at least one polycationic segment may be similarly formulated using nonionic segments such as polyetherglycols (e.g., polyethylene glycol) or copolymers of ethylene oxide and propylene oxide. See, for example, Bronstein et al., Proc. Am. Chem. Soc., Division of Polymeric Materials: Science and Engineering, 76: 52 (1997); Kabanov et al., U.S. Pat. No. 5,656,611; Spatz et al., Macromolecules, 29: 3220 (1996); Wolfert et al., Human Gene Ther., 7: 2123 (1996); Harada and Kataoka, Macromolecules, 29: 3220 (1996).

The term surfactant is used herein in a most general sense to encompass any surface active agent that is adsorbed at interface (see, for example, Martin, *Physical Pharmacy*, 4th edn., p. 370 et seq., Lea & Febiger, Philadelphia, London, 1993). These surface active agents in particular decrease the surface tension at the air-water interface in aqueous solutions (see, for example, Martin, *Physical Pharmacy*, 4th edn., p. 370 et seq., Lea & Febiger, Philadelphia, London, 1993) and include without limitation micelle forming amphiphiles, soaps, lipids, surface active drugs and other surface active biological agents, and the like (see, for example, Martin, *Physical Pharmacy*, 4th edn., Lea & Febiger, Philadelphia, London, 1993; Marcel Dekker, New York, Basel, 1979; Atwood and Florence, *J. Pharm. Pharmacol.* 1971, 23: 242S; Atwood and Florence, *J. Pharm. Sci.* 1974, 63: 988; Florence and Attwood, *Physicochemical Principles of Pharmacy*, 2nd edn., p. 180 et seq., Chapman and Hall, New York, 1988; Hunter, *Introduction to Modern Colloid Science*, p. 12 et seq., Oxford University Press, Oxford, 1993). The term cationic surfactant is used herein to encompass, without limitation any surfactant that can produce cation groups in aqueous solution. This includes, without limitation strong bases (e.g., quaternary ammonium or pyridinium salts, and the like) that dissociate in aqueous solution to form cationic groups and relatively weak bases (e.g., primary amines, secondary amines, and the like) that protonate in aqueous solution to produce a cationic group as a result of an acidic-basic reaction. Similarly, the term anionic surfactant is used herein to encompass, without limitation any surfactant that can produce anionic groups in aqueous solution. This includes, without limitation strong acids and their salts (e.g., akylsulfates, alkylsulfonates, alkylphosphonates, and the like) that dissociate in aqueous solution to form anionic groups and weak acids (e.g., carboxylic acids) that ionize in aqueous solution to produce an anionic group as a result of an acidic-basic reaction.

The charged surfactants that may be used in the practice of this invention are broadly characterized as cationic and anionic surfactants having hydrophobic/lipophilic groups, i.e., the groups poorly soluble in water, and/or revealing an ability to adsorb at water-air interface, and/or solubilize in organic solvents with low polarity and/or self-assemble in aqueous media to form a nonpolar microphase. The use of such compounds in an important feature of this invention. The interactions of hydrophobic groups of surfactant molecules with each other contribute to cooperative stabilization of the ionic complexes between the block copolymers and surfactants of the opposite charge in the compositions of the current invention, as will be further described below. Typically, the cationic surfactants will be lipophilic quaternary ammonium salts, lipopolyamines, lipophilic polyamino acids or a mixture thereof, particularly those proposed heretofore as a constituent of cationic lipid formulations for use in gene delivery. Various examples of classes and species of suitable cationic surfactants are provided hereinbelow.

Cationic surfactants that can be used in the compositions of the invention include, but are not limited to primary amines (e.g., hexylamine, heptylamine, octylamine, decylamine, undecylamine, dodecylamine, pentadecyl amine, hexadecyl amine, oleylamine, stearylamine, diaminopropane, diaminobutane, diaminopentane, diaminohexane, diaminoheptane, diaminooctane, diaminononane, diaminodecane, diaminododecane), secondary amines (e.g., N,N-distearylamine, adrenolutin, adrenalone, adrenolglomerulotropin, albuterol, azacosterol, benzoctamine, benzydamine, carazolol, cetamolol, spirogermanium), tertiary amines (e.g., N,N',N'-polyoxyethylene(10)-N-tallow-1,3-diaminopropan e, acecainide, adiphenine hydrochloride, adinozalam, ahistan, alloclamide, allocryptopyne, almitrine, amitriptyline, anileridine, aprindine, bencyclane, benoxinate, biphenamine, brompheniramine, bucumolol, bufetolol, bufotenine, bufuralol, bunaftine, bunitrolol, bupranolol, butacaine, butamirate, butethamate, butofilolol, butoxycaine, butriptyline, captodiamine, caramiphen hydrochloride, carbetapentane, carbinoxamine, carteolol, cassaidine, cassaine, cassamine, chlorpromazine, dimenoxadol, dimethazan, diphedyramine, orphenandrine, pyrilamine, pyrisuccidianol, succinylcholone iodide, tetracaine, and the like), quaternary ammonium salts, which include aromatic and non-aromatic ring-containing compounds (e.g. dodecyltrimethylammonium bromide, hexadecyltrimethylammonium bromide, alkyltrimethylammonium bromide, tetradecyltrimethylammonium bromide, benzalkonium chloride, benzethonium chloride, benzoquinonium chloride, benzoxonium chloride, bibenzonium bromide, cetalkonium chloride, cethexonium bromide, benzylonium bromide, benzyldimethyldodecylammonium chloride, benzyldimethylhexadecylammonium chloride, benzyltrimethylammonium methoxide, cetyldimethylethylammonium bromide, dimethyldioctadecyl ammonium bromide (DDAB) (see, e.g., Whitt et al., *Focus*, 1991, 13: 8), methylbenzethonium chloride, decamethonium chloride, methyl mixed trialkyl ammonium chloride, methyl trioctylammonium chloride, N-alkyl pyridinium salts, N-alkylpiperidinium salts, quinaldinium salts, amprolium, benzylpyrinium, bisdequalinium halides, azonium and azolium salts such as anisotropine methylbromide, butropium bromide, N-butylscopolammonium bromide, tetrazolium blue, quinolinium derivatives (such as atracurium besylate), piperidinium salts, such as bevonium methyl sulfate and thiazolium salts, such as beclotiamine), 1,2-diacyl-3-(trimethylammonio)propane (acyl group=dimyristoyl, dipalmitoyl, distearoyl, dioleoyl), 1,2-diacyl-3-(dimethylammonio)propane (acyl group=dimyristoyl, dipalmitoyl, distearoyl, dioleoyl), 1,2-dioleoyl-3-(4'-trimethylammonio) butanoyl-sn-glycerol, 1,2-dioleoyl-3-succinyl-sn-glycerol choline ester, cholesteryl (4'- trimethylammonio) butanoate), heterocyclic amines (e.g., azacuclonol, azaperone, azatadine, benzetimide, benziperylon, benzylmorphine, bepridil, biperidene, budipine, buphanamine, buphanitine, butaperazine, butorphanol, buzepide, calycanthine, carpipramine), imidazoles (e.g., azanidazole, azathiopropine, bifonazole, bizantrene, butacanazole, cafaminol), triasoles (e.g., bitertanol), tetrazoles (e.g., azosemide), phenothiazines (e.g., azures A, B, C), aminoglycans (e.g., daunorubicin, doxorubicin, carminomycin, 4'-epiadriamycin, 4-demethoxy-daunomycin, 11-deoxydaunorubicin, 13-deoxydaunorubicin, adriamycin-14-benzoate, adriamycin-14-actanoate, adriamycin-14-naphthaleneacetate), rhodamines (e.g. rhodamine 123), acridines (e.g. acranil, acriflavine, acrisorcin), dicationic bolaform electrolytes (C12Me6; C12Bu6), dialkylglycetylphosphorylcholine, lysolecithin), cholesterol hemisuccinate choline ester, lipopolyamines (e.g., dioctadecylamidoglycylspermine (DOGS), dipalmitoyl phosphatidylethanolamidospermine (DPPES), N'-octadecylsperminecarboxamide hydroxytrifluoroacetate, N',N"-dioctadecylspermine-carboxamide hydroxytrifluoroacetate, N'-nonafluoropentadecylsperminecarboxamide hydroxytrifluoroacetate, N',N"-dioctyl (sperminecarbonyl) glycinamide hydroxytrifluoroacetate, N'-(heptadecafluorodecyl)-N'-(nonafluoropentadecyl)-sperminecarbonyl) glycinamide hydroxytrifluoroacetate, N'-[3,6,9-trioxa-7-(2'-oxaeicos-11'-enyl) heptaeicos-18-enyl] sperminecarboxamide hydroxytrifluoroacetate, N'-(1,2-dioleoyl-sn-glycero-3-phosphoethanoyl) spermine carboxamide hydroxytrifluoroacetate) (see, for example, Behr et. al., *Proc. Natl. Acad. Sci.* 1989, 86: 6982; Remy et al., *Bioconjugate Chem.* 1994, 5: 647), 2,3-dioleyloxy-N-[2 (spermine-carboxamido) ethyl]-N,N-dimethyl-1-propanaminiumtrifluoroacetate (DOSPA) (see, for example, Ciccarone et al., *Focus* 1993, 15: 80), N,N$_I$,N$_{II}$,N$_{III}$-tetramethyl-N,N$_I$,N$_{II}$,N$_{III}$-tetrapalmitylspermine (TM-TPS) (Lukow et al., *J. Virol.* 1993, 67:4566), N-[1-(2,3-dioleyloxy)propyl]-N,N,N-trimethylamonium chloride (DOTMA) (see, for example, Felgner, et al., *Proc. Natl. Acad. Sci. USA* 1987, 84: 7413; Ciccarone et al., *Focus* 1993, 15: 80), 1,2-dioleoyl-3-dimethyl-hydroxyethyl ammonium bromide (DORI) (see, for example, Felgner et al., *J. Biol. Chem.* 1994, 269:2550), 1,2-dioleyloxypropyl-3-dimethyl-hydroxyethyl ammonium bromide (DORIE) (see, for example, Felgner et al., *J. Biol. Chem.* 1994, 269: 2550), 1,2-dioleyloxypropyl-3-dimethyl-hydroxypropyl ammonium bromide (DORIE-HP) (see, for example, Felgner et al., *J. Biol. Chem.* 1994, 269:2550), 1,2-dioleyloxypropyl-3-dimethyl-hydroxybutyl ammonium bromide (DORIE-HB) (see, for example, Felgner et al., *J. Biol. Chem.* 1994, 269: 2550), 1,2-dioleyloxypropyl-3-dimethyl-hydroxypentyl ammonium bromide (DORIE-HPe) (see, for example, Felgner et al., *J. Biol. Chem.* 1994, 269: 2550), 1,2-dimyristyloxypropyl-3-dimethyl-hydroxyethyl ammonium bromide (DMRIE) (see, for example, Felgner et al., *J. Biol. Chem.* 1994, 269: 2550), 1,2-dipalmitoyloxypropyl-3-dimethyl-hydroxyethyl ammonium bromide (DPRIE) (see, for example, Felgner et al., *J. Biol. Chem.* 1994, 269: 2550), 1,2-distearoyloxypropyl-3-dimethyl-hydroxyethyl ammonium bromide (DSRIE) (see, for example, Felgner et al., *J. Biol. Chem.* 1994, 269: 2550), N,N-dimethyl-N-[2-(2-methyl-4-(1,1,3,3-tetramethylbutyl)-phenoxy]ethoxy) ethyl]-benzenemethanaminium chloride (DEBDA), N-[1-(2, 3-dioleyloxy)propyl]-N,N,N,-trimethylammonium methylsulfate (DOTAB), lipopoly-L(or D)-lysine (see, for example, Zhou, et al., *Biochim. Biophys. Acta* 1991, 1065: 8), poly(L (or D)-lysine conjugated to N-glutarylphosphatidylethanolamine lysine (see, for example, Zhou, et al., Biochim. Biophys. Acta 1991, 1065:8), didodecyl glutamate ester with pendant amino group ($C_{12}GluPhC_nN+$) (see, for example, Behr, *Bioconjugate Chem.* 1994, 5: 382), ditetradecyl glutamate ester with pendant amino group ($C_{14}GluC_nN+$) (see, for example, Behr, *Bioconjugate Chem.* 1994, 5: 382), 9-(N',N"-dioctadecylglycinamido) acridine (see, for example, Remy et al., *Bioconjugate Chem.* 1994, 5: 647), ethyl 4-[[N-[3-bis (octadecylcarbamoyl)-2-oxapropylcarbonyl]glycinamido] pyrrole-2-carboxamido]-4-pyrrole-2-carboxylate (see, for example, Remy et al., *Bioconjugate Chem.* 1994, 5: 647), N',N'-dioctadecylornithylglycinamide hydroptrifluoroacetate (see, for example, Remy et al., *Bioconjugate Chem.* 1994, 5: 647), cationic derivatives of cholesterol (e.g., cholesteryl-3(-oxysuccinamidoethylenetrimethylammonium salt, cholesteryl-3(-oxysuccinamidoethylenedimethylamine, cholesteryl-3(-carboxyamidoethylenetrimethylammonium salt, cholesteryl-3(-carboxyamidoethylenedimethylamine, 3([N-(N',N'-dimethylaminoetane-carbomoyl]cholesterol) (see, for example, Singhal and Huang, In *Gene Therapeutics*, Wolff, Ed., p. 118 et seq., Birkhauser, Boston, 1993), pH-sensitive cationic lipids (e.g., 4-(2,3-bis-palmitoyloxy-propyl)-1-methyl-1H-imidazole, 4-(2,3-bis-oleoyloxy-propyl)-1-methyl-1H-imidazole, cholesterol-(3-imidazol-1-yl propyl) carbamate, 2,3-bis-palmitoyl-propyl-pyridin-4-yl-amine) and the like (see, for example, Budker et al., *Nature Biotechnology* 1996, 14: 760).

Especially useful in the context of gene delivery and other applications are compositions comprising mixtures of cationic surfactant and nonionic surfactants including, but not limited to dioloeoyl phosphatidylethanolamine (DOPE), dioleoyl phosphatidylcholine (DOPC) (see, for example, Felgner, et al., *Proc. Natl. Acad. Sci. USA* 1987; Singhal and Huang, In *Gene Therapeutics*, Wolff, Ed., p. 118 et seq., Birkhauser, Boston, 1993). This includes, in particular, commercially available cationic lipid compositions including but not limited to LipofectAMINE™, Lipofectine®, DMRIE-C, CellFICTIN™, LipofectACE™, Transfectam reagents (see, for example, Ciccarone et al., *Focus* 1993, 15: 80; Lukow et al., *J. Virol.* 1993, 67: 4566; Behr, *Bioconjugate Chem.* 1994, 5: 382; Singhal and Huang, In *Gene Therapeutics, Wolff, Ed., p.* 118 et seq., Birkhauser, Boston, 1993; GIBCO-BRL Co.; Promega Co., Sigma Co) and other cationic lipid compositions used for transfection of cells (see, for example, Felgner et al., *J. Biol. Chem.* 1994, 269: 2550; Budker et al., supra.

The anionic surfactants that can be used in the compositions of the present invention include, but are not limited to alkyl sulfates, alkyl sulfonates, fatty acid soaps, including salts of saturated and unsaturated fatty acids and derivatives (e.g., adrenic acid, arachidonic acid, 5,6-dehydroarachidonic acid, 20-hydroxyarachidonic acid, 20-trifluoro arachidonic acid, docosahexaenoic acid, docosapentaenoic acid, docosatrienoic acid, eicosadienoic acid, 7,7-dimethyl-5,8-eicosadienoic acid, 7,7-dimethyl-5,8-eicosadienoic acid, 8,11-eicosadiynoic acid, eicosapentaenoic acid, eicosatetraynoic acid, eicosatrienoic acid, eicosatriynoic acid, eladic acid, isolinoleic acid, linoelaidic acid, linoleic acid, linolenic acid, dihomo-γ-linolenic acid, γ-linolenic acid, 17-octadecynoic acid, oleic acid, phytanic acid, stearidonic acid, 2-octenoic acid, octanoic acid, nonanoic acid, decanoic acid, undecanoic acid, unde celenic acid, lauric acid, myristoleic acid, myristic acid, palmitic acid, palmitoleic acid, heptadecanoic acid, stearic acid, nonanedecanoic acid, heneicosanoic acid, docasanoic acid, tricosanoic acid, tetracosanoic acid, cis-15-tetracosenoic acid, hexacosanoic acid, heptacosanoic acid, octacosanoic acid, triocantanoic acid), salts of hydroxy-, hydroperoxy-, polyhydroxy-, epoxy-fatty acids (see, for example, Ingram and Brash, *Lipids* 1988, 23:340; Honn et al., *Prostaglandins* 1992, 44: 413; Yamamoto, *Free Radic. Biol. Med.* 1991, 10: 149; Fitzpatrick and Murphy, *Pharmacol. Rev.* 1989, 40: 229; Muller et al., *Prostaglandins* 1989, 38:635; Falgueyret et al., *FEBS Lett.* 1990, 262: 197; Cayman Chemical Co., 1994 Catalog, pp. 78–108), salts of saturated and unsaturated, mono- and poly-carboxylic acids (e.g., valeric acid, trans-2,4-pentadienoic acid, hexanoic acid, trans-2-hexenoic acid, trans-3-hexenoic acid, 2,6-heptadienoic acid, 6-heptenoic acid, heptanoic acid, pimelic acid, suberic acid, sebacicic acid, azelaic acid, undecanedioic acid, decanedicarboxylic 5 acid, undecanedicarboxylic acid, dodecanedicarboxylic acid, hexadecanedioic acid, docasenedioic acid, tetracosanedioic acid, agaricic acid, aleuritic acid, azafrin, bendazac, benfurodil hemisuccinate, benzylpenicillinic acid, p-(benzylsulfonamido)benzoic acid, biliverdine, bongkrekic acid, bumadizon, caffeic acid, calcium 2-ethylbutanoate, capobenic acid, carprofen, cefodizime, cefmenoxime, cefixime, cefazedone, cefatrizine, cefamandole, cefoperazone, ceforanide, cefotaxime, cefotetan, cefonicid, cefotiam, cefoxitin, cephamycins, cetiridine, cetraric acid, cetraxate, chaulmoorgic acid, chlorambucil, indomethacin, protoporphyrin IX, protizinic acid), prostanoic acid and its derivatives (e.g., prostaglandins) (see, for example, Nelson et al., *C&EN* 1982, 30–44; Frolich, *Prostaglandins*, 1984, 27: 349; Cayman Chemical Co., 1994 Catalog, pp. 26–61), leukotrienes and lipoxines (see for example, Samuelsson et al., *Science* 1987, 237: 1171; Cayman Chemical Co., 1994 Catalog, pp. 64–75), alkyl phosphates, O-phosphates (e.g., benfotiamine), alkyl phosphonates, natural and synthetic lipids (e.g., dimethylallyl pyrophosphate ammonium salt, S-farnesylthioacetic acid, farnesyl pyrophosphate, 2-hydroxymyristic acid, 2-fluorpalmitic acid, inositoltrphosphates, geranyl pyrophosphate, geranygeranyl pyrophosphate, α-hydroxyfarnesyl phosphonic acid, isopentyl pyrophoshate, phosphatidylserines, cardiolipines, phosphatidic acid and derivatives, lysophosphatidic acids, sphingolipids and like), synthetic analogs of lipids such as sodium-dialkyl sulfosuccinate (e.g., Aerosol OT®), n-alkyl ethoxylated sulfates, n-alkyl monothiocarbonates, alkyl- and arylsulfates (asaprol, azosulfamide, p-(benzylsulfonamideo) benzoic acid, cefonicid, CHAPS), mono- and dialkyl dithiophosphates, N-alkanoyl-N-methylglucamine, perfluoroalcanoate, cholate and desoxycholate salts of bile acids, 4-chloroindoleacetic acid, cucurbic acid, jasmonic acid, 7-epi jasmonic acid, 12-oxo phytodienoic acid, traumatic acid, tuberonic acid, abscisic acid, acitertin, and the like.

The preferred cationic and anionic surfactants of this invention also include fluorocarbon and mixed fluorocarbon-hydrocarbon surfactants. See, for example, Mukerjee, *P. Coll. Surfaces A: Physicochem. Engin. Asp.* 1994, 84: 1; Guo et al., *J. Phys. Chem.* 1991, 95: 1829; Guo et al., *J. Phys. Chem.*, 1992, 96: 10068. The list of such surfactants that are useful in the present invention includes, but is not limited to the salts of perfluoromonocarboxylic acids (e.g., pentafluoropropionic acid, heptafluorobutyric acid, nonanfluoropentanoic acid, tridecafluoroheptanoic acid, pentadecafluorooctanoic acid, heptadecafluorononanoic acid, nonadecafluorodecanoic acid, perfluorododecanoic acid, perfluoropolycarboxylic acids, perfluorotetradecanoic acid) and the salts of perfluoropolycarboxylic acids (e.g., hexafluoroglutaric acid, perfluoroadipic acid, perfluorosuberic acid, perfluorosebacic acid), double tail hybrid surfactants, $(C_mF_{2m+1})(C_nH_{2n+1})$CH—OSO$_3$Na (see, for example, Guo et al., *J. Phys. Chem.*, 1992, 96: 6738, Guo et al., *J. Phys. Chem.* 1992, 96: 10068; Guo et al., *J. Phys. Chem.*, 1992, 96: 10068), fluoroaliphatic phosphonates, fluoroaliphatic sulphates, and the like.

The biological agent compositions of this invention may additionally contain nonionic or zwitterionic surfactants including but not limited to phosholipids (e.g. phosphatidylethanolamines, phosphatidylglycerols, phosphatidylinositols, diacyl phosphatidylcholines, di-O-alkyl phosphatidylcholines, platelet-activating factors, PAF agonists and PAF antagonists, lysophosphatidylcholines, lysophosphatidylethanol-amines, lysophosphatidylglycerols, lysophosphatidylinositols, lyso-platelet-activating factors and analogs, and the like), saturated and unsaturated fatty acid derivatives (e.g., ethyl esters, propyl esters, cholesteryl esters, coenzyme A esters, nitrophenyl esters, naphtyl esters, monoglycerids, diglycerids, and triglycerids, fatty alcohols, fatty alcohol acetates, and the like), lipopolysaccharides, glyco- and shpingolipids (e.g. ceramides, cerebrosides, galactosyldiglycerids, gangliosides, lactocerebrosides, lysosulfatides, psychosines, shpingomyelins, sphingosines, sulfatides), chromophoric lipids (neutral lipids, phospholipids, cerebrosides, sphingomyelins), cholesterol and cholesterol derivatives, Amphotericin B, abamectin, acediasulfone, n-alkylphenyl polyoxyethylene ether, n-alkyl polyoxyethylene ethers (e.g., Triton™), sorbitan esters (e.g. Span™), polyglycol ether surfactants (Tergitol™), polyoxyethylenesorbitan (e.g., Tween™), polysorbates, polyoxyethylated glycol monoethers (e.g., Brij™, polyoxylethylene 9 lauryl ether, polyoxylethylene 10 ether, polyoxylethylene 10 tridecyl ether), lubrol, copolymers of ethylene oxide and propylene oxide (e.g., Pluronic™, Pluronic R™, Teronic™, Pluradot™), alkyl aryl polyether alcohol (Tyloxapol™), perfluoroalkyl polyoxylated amides, N,N-bis[3-D-gluconamidopropyl]cholamide, decanoyl-N-methylglucamide, n-decyl α-D-glucopyranozide, n-decyl β-D-glucopyranozide, n-decyl β-D-maltopyranozide, n-dodecyl β-D-glucopyranozide, n-undecyl β-D-glucopyranozide, n-heptyl (-d-glucopyranozide, n-heptyl β-D-thioglucopyranozide, n-hexyl β-D-glucopyranozide, n-nonanoyl β-D-glucopyranozide 1-monooleyl-rac-glycerol, nonanoyl-N-methylglucamide, n-dodecyl α-D-maltoside, n-dodecyl β-D-maltoside, N,N-bis[3-gluconamidepropyl]deoxycholamide, diethylene glycol monopentyl ether, digitonin, heptanoyl-N-methylglucamide, heptanoyl-N-methylglucamide, octanoyl-N-methylglucamide, n-octyl β-D-glucopyranozide, n-octyl α-D-glucopyranozide, n-octyl β-D-thiogalactopyranozide, n-octyl β-D-thioglucopyranozide, betaine ($R_1R_2R_3N$+ $R'CO_2$—, where $R_1R_2R_3R'$ hydrocarbon chains), sulfobetaine ($R_1R_2R_3N$+$R'SO_3$—), phoshoplipids (e.g. dialkyl phosphatidylcholine), 3-[(3-cholamidopropyl)-dimethylammonio]-2-hydroxy-1-propanesulfonate, 3-[(3-cholamidopropyl)-dimethylammonio]-1-propanesulfonate, N-decyl-N,N-dimethyl-3-ammonio-1-propanesulfonate, N-dodecyl-N,N-dimethyl-3-ammonio-1-propanesulfonate, N-hexadecyl-N,N-dimethyl-3-ammonio-1-propanesulfonate, N-octadecyl-N,N-dimethyl-3-ammonio-1-propanesulfonate, N-octyl-N,N-dimethyl-3-ammonio-1-propanesulfonate, N-tetradecyl-N,N-dimethyl-3-ammonio-1-propanesulfonate, dialkyl phosphatitidylethanolamine.

The biological agents that may be used in the practice of this invention include those having utility in diagnostics or imaging, as well as those capable of acting on a cell, organ or organism to create a change in the functioning of the cell, organ or organism, including but not limited to pharmaceutical agents. Such biological agents include a wide variety of substances that are used in diagnostics, therapy, immunization or otherwise are applied to combat human and animal disease. Such agents include but are not limited to analgesic agents, anti-inflamatory agents, antibacterial agents, antiviral agents, antifungal agents, antiparasitic agents, tumoricidal or anti-cancer agents, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, anti-glaucomic agents, mydriatic compounds and local anesthetics.

The biological agent compositions of this invention may comprise polyions, e.g., either polycations, if they have more than about ten negative charges, or polyanions, if they have more than about ten negative charges. Examples of polycations include cationic polypeptides, examples of polyanions include polynucleotides. It is important, however, to note that there is a fundamental limitation to the charge sign of the polyionic biological agents used in the composition of this invention with block copolymers and surfactants. The polyanionic biological agent must not (1) have the opposite charge compared to the charge sign of the P-type segment of the block copolymer, and (2) have the same charge sign compared to the charge sign of the surfactant. That is if the P-type segment of the block copolymer is a polyanion and surfactant is cationic, then the biological agent must not be a polycation. Similarly, if the P-type segment of the block copolymer is a polycation and surfactant is anionic, then the biological agent must not be a polyanion. The reason for such limitation is the necessity to avoid competitive binding of the polyion biological agent and surfactant of the same charge to the P-type segment of the block copolymer. Normally, the polyanionic biological agent would have comparable or higher affinity to the oppositely charged P-type segment of the block copolymer when compared to the surfactant. The competition between the polyion biological agent and the surfactant of the same charge for the electrostatic binding with the P-type segment of the opposite charge would disturb the electrostatic interactions between the surfactant and the block copolymer and result in the destruction of the compositions of the current invention. For example, if polylysine having 10 repeating units is added to the complex formed between polyethylene oxide-block-poly(sodium methacrylate) block copolymer and cetylpyridnium bromide, then the substitution reaction takes places resulting in the disintegration of the complex between the block copolymer and surfactant. Similarly, if a 10-mer oligonucleotide is added to the complex formed between polyethylene oxide-block-polyethyleneimine block copolymer and Aerosol OT, then this complex disintegrates as a result of the substitution reaction.

The biological agents which may be used in the compositions of the invention may include, but are not limited to non-steroidal anti-inflamatories, such as indomethacin, salicylic acid acetate, ibuprofen, sulindac, piroxicam, and naproxen, antiglaucomic agents such as timolol or pilocarpine, neurotransmitters such as acetylcholine, anesthetics such as dibucaine, neuroleptics such as the phenothiazines (e.g., compazine, thorazine, promazine, chlorpromazine, acepromazine, aminopromazine, perazine, prochlorperazine, trifluoperazine, and thioproperazine), rauwolfia alkaloids (e.g., reserpine and deserpine), thioxanthenes (e.g., chlorprothixene and tiotixene), butyrophenones (e.g., haloperidol, moperone, trifluoperidol, timiperone, and droperidol), diphenylbutylpiperidines (e.g., pimozde), and benzamides (e.g., sulpiride and tiapride); tranquilizers such as glycerol derivatives (e.g., mephenesin and methocarbamol), propanediols (e.g., meprobamate), diphenylmethane derivatives (e.g., orphenadrine, benzotrapine, and hydroxyzine), and benzodiazepines (e.g., chlordiazepoxide and diazepam); hypnotics (e.g., zolpdem and butoctamide); beta-blockers (e.g., propranolol, acebutonol, metoprolol, and pindolol); antidepressants such as dibenzazepines (e.g., imipramine), dibenzocycloheptenes (e.g., amtiriptyline), and the tetracyclics (e.g., mianserine); MAO inhibitors (e.g., phenelzine, iproniazid, and selegeline); psychostimulants such as phenylehtylamine derivatives (e.g., amphetamines, dexamphetamines, fenproporex, phentermine, amfeprramone, and pemoline) and dimethylaminoethanols (e.g., clofenciclan, cyprodenate, aminorex, and mazindol); GABA-mimetics (e.g., progabide); alkaloids (e.g., codergocrine, dihydroergocristine, and vincamine); anti-Parkinsonism agents (e.g., L-dopamine and selegeline); agents utilized in the treatment of Altzheimer's disease, cholinergics (e.g., citicoline and physostigmine); vasodilators (e.g., pentoxifyline); and cerebro active agents (e.g., pyritinol and meclofenoxate).

Anti-neoplastic agents can also be used advantageously as biological agents in the compositions of the invention. Representative examples include, but are not limited to paclitaxel, daunorubicin, doxorubicin, carminomycin, 4'-epiadriamycin, 4-demethoxy-daunomycin, 11-deoxydaunorubicin, 13-deoxydaunorubicin, adriamycin-14-benzoate, adriamycin-14-actanoate, adriamycin-14-naphthaleneacetate, vinblastine, vincristine, mitomycin C, N-methyl mitomycin C, bleomycin $A_2$, dideazatetrahydrofolic acid, aminopterin, methotrexate, cholchicine and cisplatin. Representative antibacterial agents are the aminoglycosides including gentamicin. Representative antiviral compounds are rifampicin, 3'-azido-3'-deoxythymidine (AZT), and acylovir. Representative antifungal agents are the azoles, including fluconazole, macrolides such as amphotericin B, and candicidin. Representative anti-parastic compounds are the antimonials. Suitable biological agents also include, without limitation vinca alkaloids, such as vincristine and vinblastine, mitomycin-type antibiotics, such as mitomycin C and N-methyl mitomycin, bleomycin-type antibiotics such as bleomycin $A_2$, antifolates such as methotrexate, aminopterin, and dideaza-tetrahydrofolic acid, taxanes, anthracycline antibiotics and others. The compositions also can utilize a variety of polypeptides, such as antibodies, toxins, such as diphtheria toxin, peptide hormones, such as colony stimulating factor, and tumor necrosis factors, neuropeptides, growth hormone, erythropoietin, and thyroid hormone, lipoproteins such as μ-lipoprotein, proteoglycans such as hyaluronic acid, glycoproteins such as gonadotropin hormone, immunomodulators or cytokines such as the interferons or interleukins, as well as hormone receptors such as the estrogen receptor.

The compositions also can comprise enzyme inhibiting agents such as reverse transcriptase inhibitors, protease inhibitors, angiotensin converting enzymes, 5μ-reductase, and the like. Typical of these agents are peptide and non-peptide structures such as finasteride, quinapril, ramipril, lisinopril, saquinavir, ritonavir, indinavir, nelfinavir, zidovudine, zalcitabine, allophenylnorstatine, kynostatin, delaviridine, bis-tetrahydrofuran ligands (see, for example Ghosh et al., *J. Med. Chem.* 1996, 39: 3278), and didanosine. Such agents can be administered alone or in combination therapy; e.g., a combination therapy utilizing saquinavir, zalcitabine, and didanosine, zalcitabine, and zidovudine. See, for example, Collier et al., *Antiviral Res.* 1996, 29: 99.

The biological agent compositions can also comprise nucleotides, such as thymine, nucleic acids, such as DNA or RNA, or synthetic oligonucleotides, which may be derivatized by covalently modifying the 5' or the 3' end of the polynucleic acid molecule with hydrophobic substituents to facilitate entry into cells (see for example, Kabanov et al., *FEBS Lett.* 1990, 259, 327; Kabanov and Alakhov, *J. Contr. Rel.* 1990, 28: 15). Additionally, the phosphate backbone of the polynucleotides may be modified to remove the negative charge (see, for example, Agris et al., *Biochemistry* 1968, 25:6268, Cazenave and Helene in *Antisense Nucleic Acids and Proteins: Fundamentals and Applications*, Mol and Van der Krol, Eds., p. 47 et seq., Marcel Dekker, New York, 1991), or the purine or pyrimidine bases may been modified, for example, to incorporate photo-induced crosslinking groups, alkylating groups, organometallic groups, intercalating. groups, biotin, fluorescent and radioactive groups (see, for example, *Antisense Nucleic Acids and Proteins: Fundamentals and Applications*, Mol and Van der Krol, Eds., p. 47 et seq., Marcel Dekker, New York, 1991; Milligan et al., In *Gene Therapy for Neoplastic Diseases*, Huber and Laso, Eds. P. 228 et seq., New York Academy of Sciences, New York, 1994). Such nucleic acid molecules can be among other things antisense nucleic acid molecules, phosphodiester, oligonucleotide α-anomers, ethylphospotriester analogs, phosphorothicates, phosphorodithioates, phosphoroethyletriesters, methylphosphonates, and the like (see, e.g., Crooke, *Anti-Cancer Drug Design* 1991, 6: 609; De Mesmaeker et al, *Acc. Chem . Res.* 1995, 28: 366). The compositions of the invention may also include antigene, ribozyme and aptamer nucleic acid drugs (see, for example, Stull and Szoka, *Pharm. Res.* 1995, 12: 465).

Included among the suitable biological agents are viral genomes and viruses (including the lipid and protein coat). Thus, formulation of the above-described compositions to include a variety of viral vectors, including complete viruses of their parts, for use in gene delivery (e.g. retroviruses, adenoviruses, herpes-virus, Pox-virus) is contemplated to be within the scope of this invention. See, for example, Hodgson, Biotechnology, 1995, 13: 222.

Other suitable biological agents include oxygen transporters (e.g. porphines, porphirines and their complexes with metal ions), coenzymes and vitamins (e.g. NAD/NADH, vitamins B12, chlorophylls), and the like.

Suitable biological agents further include those used in diagnostics visualization methods, such as magnetic resonance imaging (e.g., gadolinium (III) diethylenetriamine pentaacetic acid), and may be a chelating group (e.g., diethylenetriamine pentaacetic acid, triethylenetriamine pentaacetic acid, ethylenediamine-tetraacetic acid, 1,2-diaminocyclo-hexane-N,N,N',N'-tetraaceticacid, N,N'-di(2-hydroxybenzyl) ethylene diamine), N-(2-hydroxyethyl) ethylene diamine triacetic acid and the like). Such biological agent may further include an alpha-, beta-, or gamma-emitting radionuclide (e.g., galliun 67, indium 111, technetium 99). Iodine-containing radiopaque molecules are also suitable diagnostic agents. The diagnostic agent may also include a paramagnetic or superparamagnetic element, or combination of paramagnetic element and radionuclide. The paramagnetic elements include but are not limited to gadolinium (III), dysporsium (III), holmium (III), europium (III) iron (III) or manganese (II).

The composition may further include a targeting group including but not limited to antibody, fragment of an antibody, protein ligand, polysaccharide, polynucleotide, polypeptide, low molecular mass organic molecule and the like. Such targeting group can be linked covalently to the block copolymer or surfactant, or can be non-covalently incorporated in the compositions through hydrophobic, electrostatic interactions or hydrogen bonds.

While not wishing to be bound by any particular theory, it is believed that the above-described surfactants and block copolymers of opposite charge form stable complexes due to cooperative binding. (See, e.g., Goddard, In *Interactions of Surfactants with Polymers and Proteins*. Goddard and Ananthapadmanabhan, Eds., pp. 171 et seq., CRC Press, Boca Raton, Ann Arbor, London, Tokyo, 1992). Cooperative binding occurs in the sense that binding of surfactant molecules to the block copolymer is enhanced by the presence of other molecules of the same or a different surfactant already bound to the same copolymer. According to the cooperative binding mechanism which is believed to underlie this invention, surfactant binds electrostatically to the oppositely charged P-type segments of the block copolymer to form supramolecular complexes. These complexes are cooperatively stabilized by the interactions of the hydrophobic parts of surfactant molecules bound to the same P-type segment with each other. Indeed, it appears that without these hydrophobic interactions, formation of the desired complex would not occur. FIG. 1 presents the binding isotherms for interaction of cetylpyridinium bromide and dodecylpyridinium bromide with the polyethylene oxide-block-poly(sodium methacrylate) block copolymer. As can be seen in FIG. 1, a decrease in the length of the hydrophobic substituent on the surfactant, from more hydrophobic cetyl- to less hydrophobic dodecyl-, decreases the stability of the complex more than ten-fold. This binding mechanism is, in particular, characteristic for surface active biological agents. See, for example, Florence and Attwood, *Physicochemical Principles of Pharmacy*, 2nd edn., p.180 et seq., Chapman and Hall, New York, 1988).

Figure 2:
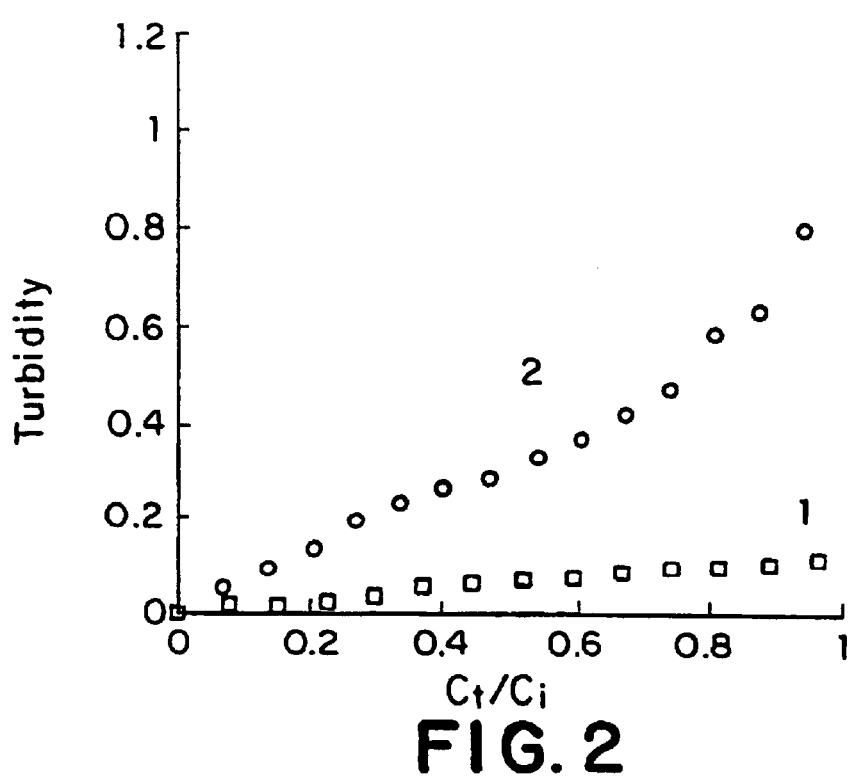
FIG. 2 is a graphical representation showing turbidity in mixtures of cetylpyridinium bromide and polyethylene oxide-block-poly(sodium methacrylate) (1) and cetylpyridinium bromide and poly(sodium methacrylate) (2), as a function of the composition of the mixture.

Formation of the electrostatic complexes between surfactants and P-type segments results in charge neutralization. As a result hydrophobicity of the complexed segments increases and aqueous solubility decreases. However, the preferred biological agent compositions remain in the aqueous solution due to the presence of the N-type segments linked to the P-type segments. By varying the relative lengths and amounts of the N-type and P-type blocks it is possible to vary the hydrophilic/lipophilic properties of the complexes formed between the surfactant and block copolymer and to optimize the solubility of the preferred compositions. It is preferred that the compositions of the present invention are water soluble at physiological conditions (pH, osmomolarity, etc.) and temperatures. FIG. 2 shows that binding of cetylpyridinium bromide to poly(sodium methacrylate) segment alone results in formation of a water-insoluble complex, whereas binding of the same surfactant to the block copolymer polyethylene oxide-block-poly (sodium methacrylate) yields a water-soluble complex.

The compositions of the present invention normally form complexes of small size that are thermodynamically stable and do not aggregate after storing in solutions for a period of time on the order of weeks or months, depending on the type of polymer present therein. The ability to produce particles of such limited size is important because small particles can easily penetrate into tissues through even small capillaries and enter cells via endocytosis. The preferred size of these particles is less than 500 nm, more preferred less than 200 nm, still more preferred less than 100 nm. These systems can be lyophilized and stored as a lyophilized powder and then re-dissolved to form solutions with the particles of the same size.

It is useful to consider the constituents that make up the complexes of this invention in terms of a parameter referred to herein as charge ratio of the complex. The charge ratio of the complex, herein designated as "$\phi$", is the ratio of the net charge of the surfactant molecules bound with one block copolymer molecule to the net charge of the P-type segments in this block copolymer. By way of example, if the surfactant molecule has two positively charged groups and five negatively charged groups, it has a "net charge" of −3. Thus, if a surfactant with the net charge $z_1$ binds to the oppositely charged P-type segments of the block copolymer, then the charge ratio is expressed as follows:

$$\phi = \frac{n \cdot z_1}{\gamma \cdot z_2 \cdot PD} \quad (1)$$

where n is the number of surfactant molecules bound to one block copolymer molecule, $z_2$ is the net charge of the repeating unit of the P-type segment, PD is the degree of polymerization of the P-type segment, and $\gamma$ is the number of P-type segments in the block copolymer molecule.

Figure 3A:
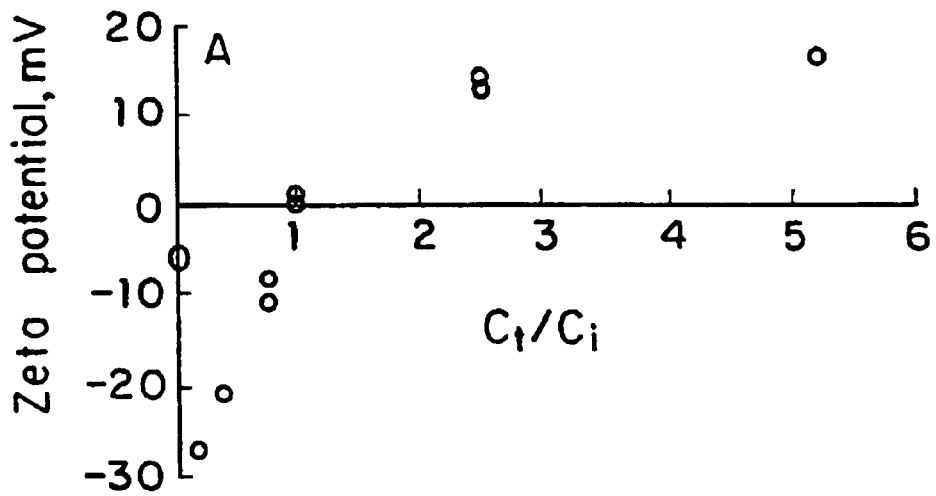
FIG. 3 graphically illustrates the zeta potential (FIG. 4a) and effective diameter (FIG. 4b) of particles formed in the mixture of cetylpyridinium bromide and poly(sodium methacrylate) at various ratios of the surfactant to the ionic units of block copolymer.
Figure 3B:
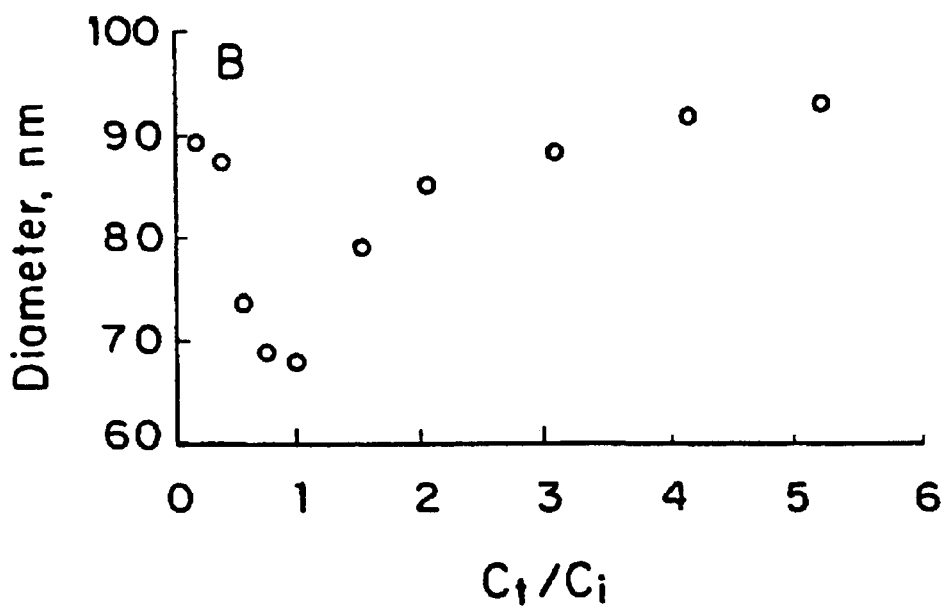

If $\phi<1$, then the complex has the same charge sign as the P-type segments; if $\phi>1$, the complex has the same charge sign as the surfactant; and if $\phi=1$, the complex is electroneutral. Therefore, by varying the molar ratio of the components in the compositions the charge of the particles formed can be changed form negative to positive and vise versa. See for example FIG. 3. As a result various biological agents can be incorporated into such particles through combination of electrostatic and hydrophobic interactions. For example, the compositions from cationic biological agents (e.g., cholesteryl (4'-trimethyl ammino) butanoate and anionic block copolymer (e.g., polyethylene oxide-block-poly(sodium methacrylate)) at $\phi>1$ are positively charged and incorporate negatively charged polynucleotide molecules through electrostatic interactions. The compositions from anionic biological agents (e.g., Aerosol® OT) and cationic copolymer (e.g., polyethyleneimine and polyethylene oxide) at $\phi>1$ are negatively charged and incorporate positively charged polypeptide molecules through electrostatic interactions.

As previously noted, in the case of a composition including an anionic block copolymer and a positively charged therapeutic or diagnostic, the net charge of the latter should be no more than about 10, and preferably about 5. Likewise, in the case of a composition including a cationic block copolymer, and a negatively charged therapeutic or diagnostic agent, the net charge of the latter should be no more than about 10, and preferably about 5.

It is further useful to introduce the parameter characterizing the ratio of the net charges of surfactant to the net charges of the P-type segments of the block copolymer in the compositions of this invention. This parameter referred herein as composition of the mixture, and herein designated "Z" is expressed as follows:

$$Z = \frac{z_1 \cdot C_1}{\gamma \cdot z_2 \cdot PD \cdot C_2} \quad (2)$$

where $z_1$, $z_2$, $\gamma$, and PD have the same meaning as in equation (1) and $C_1$ and $C_2$ are the molar concentrations of the surfactant and block copolymer in the mixture. While not wishing to be bound to any particulate theory, it is believed that the relationship between the charge ratio of the complex and composition of the mixture is as follows, $\phi \geq Z$. This means that $n \geq C_1 C_2$, i.e., the number of surfactant molecules bound to one block copolymer molecule is not less that the ratio of the molar concentrations of the surfactant and copolymer in the mixture. Further, when Z is less than 1, preferably less than 0.5, $n > C_1 C_2$, i.e., the number of surfactant molecules bound to one block copolymer molecule is more than the ratio of the molar concentrations of the surfactant and block copolymer in the mixture. The reason for the behavior expressed by those relationships is that the binding of surfactant molecules to the P-type segments of the block copolymer is enhanced by the presence of the molecules of surfactant already bound to the same block copolymer. Therefore, those relationships reflect the cooperative binding mechanism between the surfactant and block copolymers of the current invention.

Under certain conditions the particles of the complex spontaneously form vesicles that contain an internal volume defined by the constituents of the complex. Various biologically active agents (for example, 3'-azido-3'-deoxythymidine, water soluble protease inhibitors, interleukins, insulin and the like) can be physically entrapped into the internal aqueous volume of such vesicles. The optimal conditions for the vesicle formation is determined by the composition of the mixture, so that the vesicles form when Z is more than about 0.1 and less than 100, preferably more than 0.4 and less than 20, still more preferbly more than 0.7 less than 10.

Furthermore, the compositions of present invention can solubilize hydrophobic biological agents (e.g., paclitaxel) through nonpolar interactions in the microphase formed by the hydrophobic groups of the surfactant.

Figure 4:
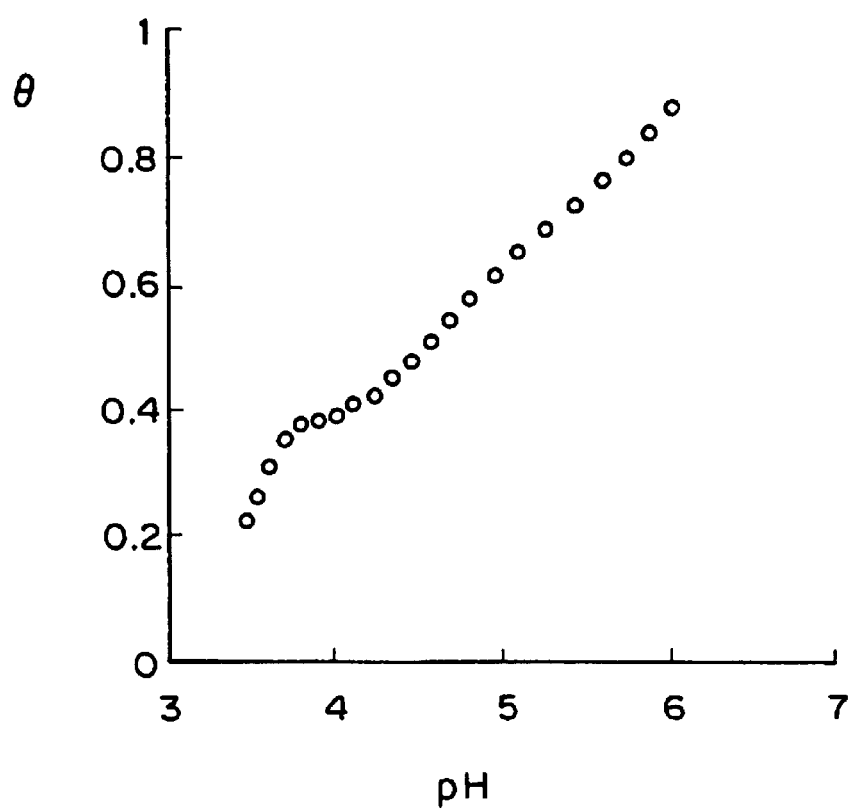
FIG. 4 shows the dependence of the degree of conversion in the polyion coupling reaction for the mixture of cetylpyridinium bromide and polyethylene oxide-block-polymethacrylic acid.

One important aspect of the current invention is that electrostatic interactions between the charged groups of the biologically active surface active agent and repeating units of the P-type segments of the block copolymer are pH-dependent. For example, FIG. 4 shows the pH-dependency of the reaction between cetylpyridinium bromide and the copolymer of polymethacrylic acid and polyethylene oxide. It is preferred that either the P-type segment of the block copolymer or the surfactant or both the P-type segment and the surfactant represent a weak acid or weak base. The preferred compositions formed are pH-dependent in the pH-range of from about pH 2.0 to about pH 10.0, more preferably in the pH-range of from about pH 3.0 to about pH 9.0, still more preferably in the pH-range of from about pH 4.0 to about pH 8.0. Dissociation of the biologically active surfactant and block copolymer complexes as a result of the pH change is characterized by step-type behavior, with more cooperative systems revealing sharper pH dependencies. Preferably these complexes dissociate when the pH change is about 3.0 units of pH, more preferably about 2.0 units of pH, still more preferably about 1.0 unit of pH. Since the biologically active surfactant and block copolymer are linked to each other through non-covalent interactions, dissociation of the complex results in the release of the biological agent. The complexes between the surfactants and block copolymers are stable in the pH range of from about pH 5.5 to about pH 8.5, preferably in the pH range of from about pH 6.5 to about pH 7.5. These complexes, however, easily dissociate when the pH shift occurs in the target tissue or cell, or other target site, which enables site-specific release of the biological agents. To facilitate for the release of the surfactant active biological agent from the compositions of the first embodiment the total amount of net charge of these biological agents is no more than about 5, more preferably no more than 4, still more preferably no more than 3.

The compositions of the present invention allow diverse routes of administration, including but not limited by parenteral (such as intramuscular, subcutaneous, intraperitoneal, and intravenous), oral, topical, otic, topical, vaginal, pulmonary, and ocular. These compositions can take the form of tablets, capsules, lozenges, troches, powders, gels, syrups, elixirs, aqueous solutions, suspensions, micelles, emulsions and microemulsions.

Conventional pharmaceutical formulations are employed. In the case of tablets, for example, well-known carriers such as lactose, sodium citrate, and salts of phosphoric acid can be used. Disintegrants such as starch, and lubricating agents such as magnesium stearate, sodium lauryl sulfate and talc, as are commonly used in tablets, can be present. Capsules for oral administration can include diluents such as lactose and high molecular weight polyethylene glycols. When aqueous suspensions are required for oral use, the conjugate can be combined with emulsifying and suspending agents. For parenteral administration, sterile solutions of the conjugate are usually prepared, and the pH of the solutions are suitably adjusted and buffered. For intravenous use, the total concentration of solutes should be controlled to render the preparation isotonic. For ocular administration, ointments or droppable liquids may be delivered by well-known ocular delivery systems such as applicators or eyedroppers. Such compositions can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. For pulmonary administration, diluents and/or carriers will be selected to be appropriate to allow for formation of an aerosol.

The following examples are provided to describe the invention in further detail. These examples are intended merely to illustrate specific embodiments of the present invention and should in no way be construed as limiting the invention.

EXAMPLE 1

A. Block copolymer of tert-butyl methacrylate and ethylene oxide used in this study was prepared by sequential anionic polymerization generally following the previously published procedure (Wang et al., *J. Polym. Sci., Part A: Polym. Chem.* 1992, 30: 2251). The block lengths in copolymer were 176 for the PEO and 186 for tert-butyl methacrylate segments respectively. This copolymer was hydrolyzed to obtain the polyethylene oxide-block-polymethacrylic acid as described by Wang et al. (*J. Polym. Sci., Part A: Polym. Chem.* 1992, 30: 2251). The polyethylene oxide-block-poly (sodium methacrylate) was prepared by redissolving the acid form of the copolymer in tetrahydrofurane : methanol mixture (95:5 v/v) and adding NaOH in methanol. The precipitate containing polyethylene oxide-block-poly (sodium methacrylate) was filtered and washed with methanol, then redissolved in water and freeze dried. The concentration of carboxylate groups in the copolymer sample was estimated by potentiometric titration.

B. The binding isotherms of cetylpyridinium bromide (Sigma Co.) and dodecylpyridinium bromide (Sigma Co.) with the polyethylene oxide-block-poly(sodium methacrylate) copolymer were determined potentiometrically by using the following ion-selective electrode: Ag/AgCl | 1 M $NH_4NO_3$ agar bridge | reference solution (surfactant, $2.5 \cdot 10^{-4}$ M) | PVC membrane | sample solution | 1 M $NH_4NO_3$ agar bridge | Ag/AgCl. The preparation of PVC ion-selective electrode is described elsewhere (Shirahama et al., *Bull. Chem. Soc. Jpn.* 1981, 54: 375; Shirahama and Tashiro, *Bull. Chem. Soc. Jpn.* 1984, 57: 377; Mel'nikov et al., *J. Am. Chem. Soc.* 1995, 117: 9951). The electromotive force (emf) of the cell was measured with a digital Radiometer pHM-83 pH-meter. The electrode exhibited a good Nernstian response over the range of surfactant concentrations examined. Binding isotherms were obtained by titration of $5'10^{-4}$ base-mole/L polyethylene oxide-block-poly(sodium methacrylate) solutions with the solution of the corresponding surfactant. The results were corrected for the decrease in the copolymer concentration as a result of the addition of the surfactant solution. The fraction of occupied binding sites β was defined as follows $$\beta=(C_t-C_f)/C_i \quad (3)$$

where $C_t$ is the total concentration of added surfactant, $C_f$ is the concentration of the free surfactant, $C_f$ determined using the calibration curves (i.e., linear plots "emf vs. log $C_t$" determined in the absence of polymer and $C_t$<CMC), and $C_i$ is the concentration of ionic groups of the block copolymer. The results obtained for binding of cetylpyridinium bromide and dodecylpyridinium bromide are presented in FIG. 1.

EXAMPLE 2

Polyethylene oxide-block-poly(sodium methacrylate) was the same as described in Example 4. The homopolymer polymethacrylic acid with a Pw=930 was obtained by radical polymerization (Lipatov, and Zubov, Vysokomol. Soedin., Ser. A. 1959, 1:88). Complexes formed between these polymers and cetylpyridinium bromide (Sigma Co.) were studied using turbidity measurements. At base molar concentrations of anionic polymers $1.08.10^{-3}$ base-mole/L; temperature 25° C., and pH 9.2. The turbidity measurements were carried out using a Shimadzu UV160 spectrophotometer at 420 nm after equilibration of the system typically for 3 minutes. The data are reported in FIG. 2 as (100-T)/100, where T is transmission (%) for complexes from polyethylene oxide-block-poly(sodium methacrylate) and poly (sodium methacrylate).

EXAMPLE 3

The complexes between N-cetylpyridinium bromide and polyethylene oxide-block-poly(sodium methacrylate) were prepared in $8 \cdot 10^{-4}$ base-mole/L solution of the block copolymer at 25° C. and pH 9.2. The Ct/Ci was varied from 0.01 to 5, where $C_t$ is the total concentration of added surfactant, and $C_i$ is the concentration of ionic groups of the block copolymer. Electrophoretic mobility (EPM) measurements were performed at 25° C. with an electric field strength of 15–18 V/cm by using "ZetaPlus" Zeta Potential Analyzer (Brookhaven Instrument Co.) with 15 mV solid state laser operated at a laser wavelength of 635 nm. The zeta-potential of the particles was calculated from the EPM values using the Smoluchowski equation. Effective hydrodynamic diameter was measured by photon correlation spectroscopy using the same instrument equipped with the Multi Angle Option. All solutions were prepared using double distilled water and were filtered repeatedly through the Millipore membrane with pore size 0.22 µM. The sizing measurements were performed at 25° C. at an angle of 90°. The results are presented in FIG. 3.

EXAMPLE 4

The interaction between a cationic surfactant (S+) and a weak polyacid represents an ion exchange reaction resulting in the release of the protons in accordance with the following scheme:

$$(|\text{—COOH})_n + nS+ <=> [|\text{—COO—S}+]_n + nH+ \quad (4)$$

The equilibrium of this reaction for the mixtures of cetylpyridinium bromide with polyethylene oxide-block-poly methacrylic acid was studied at different pH by potentiometric titration (see, for example, Kabanov, Polymer Science 1994, 36:143). Polyethylene oxide-block-poly methacrylic acid was synthesized as described in Example 1. The alkali titration curves were obtained for the mixtures of N-cetylpyridinium bromide (Sigma Co.) with polyethylene oxide-block-poly methacrylic acid. The total concentration of the surfactant was equal to the concentration of the ionizable groups of the polyacid. The degree of conversion, θ, in the ion exchange reaction (5) was determined from original titration curves on the assumption that all alkali is consumed for neutralization of protons released as a result of this reaction. For a weak polyacid θ at a given pH is expressed as follows $$\theta = (m_b/V + [H^+] - \sqrt{K_a C_o})/C_o, \quad (5)$$

where $M_b$ is the number of moles of the added base, V is the current volume of the reaction system, $K_a$ is the characteristic dissociation constant, $C_o$ is the base-molar concentration of the polyacid. The results are presented in FIG. 4.

EXAMPLE 5

The existence of internal aqueous volume in the particles of the complex formed between the block copolymers and surfactants of the present invention can be conveniently demonstrated using a water-soluble fluorescent dye, 5,6-carboxyfluorescein. See, for example, Parker, Photoluminiscence of Solutions; Elsevier: N.Y., p.303 et seq., 1968. The complex between N-cetylpyridinium bromide and polyethylene oxide-block-poly(sodium methacrylate) is prepared as described in Example 3 at Ct/Ci=1 replacing the solution of the copolymer in water for the solution of the same copolymer in 10 mM of 5,6-carboxyfluorescein (Sigma Co.). Briefly, 0.87 ml of the aqueous solution of 10 mM 5,6-carboxyfluorescein, pH 7.4 is mixed with 50 μl of 0.039 M solution of polyethylene oxide-block-poly(sodium methacrylate) and 80 μl of 0.025 M N-cetylpyridinium bromide solution. After 30 minutes incubation at room temperature the particles of the complex were separated from the dye remaining in the external volume by gel permeation chromatography using Sephadex G-25 medium (Pharmacia Biotech) equilibrated with the solution of 0.01 mM N-cetylpyridinium bromide. The fluorescence emission of 5,6-carboxyfluorescein in the solutions obtained is determined at the excitation wavelength 495 nm and 25° C. using Shimadzu 5000 spectrofluorimeter. The maximum of fluorescence emission of the dye in this system was observed at 517.2 nm (slit 1.5 nm) which corresponds to the emission maximum of the free dye in the absence of the particles. Addition of 40 μl of 10% (v/v) aqueous Triton X-100 (Sigma Co.) to this system results in a sharp increase in the fluorescence intensity resulting from the release of the concentrated dye from the internal aqueous cavity of the particles. This suggests that the particles represent the vesicles with an internal aqueous volume.

EXAMPLE 6

The complex between N-cetylpyridinium bromide and polyethylene oxide-block-poly(sodium methacrylate) was prepared as described in Example 5 replacing 10 mM 5,6-carboxyfluorescein solution with 0.1 mM solution of calcein (Sigma Co.). The particles of this complex were separated by gel permeation chromatography as described in Example 5. The fluorescence emission intensity of calcein was determined at the emission and excitation wavelengths 490 nm and 520 nm respectively. 2 μl of $CoCl_2$ solution and 40 μl of 10% Triton X-100 were added to this system in different order to quench fluorescence outside the vesicles. Addition of $CoCl_2$ resulted in the decrease of the fluorescence in this system to 3% of the initial fluorescence. When Triton X-100 was added after $CoCl_2$ the fluorescence was further decreased to 1% of the initial value. In contrast, when Triton X-100 was added without prior addition of $CoCl_2$ no change in the fluorescence was recorded. When $CoCl_2$ solution was added after the Triton X-100 solution the fluorescence was decreased to about 1% of the initial value. This suggests formation of the vesicles with an internal volume of about 2% of the total volume.

EXAMPLE 7

The complex between N-cetylpyridinium bromide and polyethylene oxide-block-poly(sodium methacrylate) is prepared as described in Example 5 replacing 10 mM 5,6-carboxyfluorescein solution with 1 μM solution of alkaline phosphatase (Sigma Co.). The vesicles are separated from the external solution by gel permeation chromatography using Sephadex G-25 medium (Pharmacia Biotech) equilibrated with the solution of 0.01 mM N-cetylpyridinium bromide. The amount of alkaline phosphatase incorporated into the vesicles is determined enzymatically using p-nitrophenyl phosphate (Sigma Co.) as a substrate (Larsson, Immunochemistry: Theory and Practice, CRC Press, Boca Raton, Fla., 1988). This assay reveals that about 1% of protein incorporates into the vesicles.

EXAMPLE 8

The complex between N-cetylpyridinium bromide and polyethylene oxide-block-poly(sodium methacrylate) is prepared as described in Example 2 replacing 10 mM 5,6-carboxyfluorescein solution for 1 μM solution of acridin-labeled 20-mer phosphodiester oligonucleotide synthesized as described by Vinogradov, et al., Biochem. Biophys. Res. Commun. 1994, 203: 959. The fraction of oligonucleotide incorporated into the vesicles determined by acridine is 75% of initial.

EXAMPLE 9

A polyethyleneglycol (8,000)-polyethylene imine (m.w. 2,000) copolymer was synthesized as previously reported by Vinogradov et al. (Pharm. Res., 14: S-641).

A complex between the polyethylene glycol-polyethyleneimine copolymer and anionic surfactant, Aerosol(OT(Sigma Co.) was obtained at $C_t/C_i=1$, where $C_t$ is the total concentration of added surfactant, and $C_i$ is the concentration of ionic groups of the block copolymer. The size of the particles formed, determined by dynamic light scattering as described in Example 3, above equals 57 nm.

EXAMPLE 10

The complex between the polyethylene glycol-polyethyleneimine copolymer, exemplified above, and fatty acid salt, oleic acid sodium salt (Sigma Co.) was obtained at $C_t-C_i=1$ in sodium phosphate buffer (SPB), 10 mM, pH 6.0 by simple mixing of the copolymer solution in the same buffer and fatty acid salt solution in methanol. The final content of methanol in the complex solution was 3%. The size of the particles formed, determined by dynamic light scattering as described in Example 3, above, was 54 nm.

EXAMPLE 11

The complex between the polyethylene glycol-polyethyleneimine copolymer, mentioned above, and fatty acid salt, oleic acid sodium salt was obtained at $C_t–C_i=1$ in sodium phosphate buffer (SPB), 10 mM, pH 7.4, as described in Example 10, above. The size of the particles formed, determined by dynamic light scattering as described in Example 3, above, was 44 nm.

EXAMPLE 12

The complex between the polyethylene glycol-polyethyleneimine copolymer, mentioned above, and fatty acid salt, oleic acid sodium salt was obtained at $C_t–C_i=1$ in TRIS-buffer, 10 nM, pH 8.2, as described in Example 10, above. The size of the particles formed, determined by dynamic light scattering as described in Example 3, above, was 56 nm.

EXAMPLE 13

The complex between the polyethylene glycol-polyethyleneimine copolymer and retinoic acid (Aldrich Co.) was obtained at $C_t–C_i=1$ in sodium phosphate buffer (SPB), 10 mM, pH 7.4. The solution of retinoic acid in water/methanol (60:40, v/v) mixture containing sodium hydroxide was added to the copolymer solution in the SPB. The final content of methanol in the complex solution was 5%. The additional absorption band ($\lambda_{max}=306$ nm) in the UV-vis spectrum of retinoic acid in the presence of copolymer was found to be comparable to that of pure retinoic acid at the same conditions ($\lambda_{max}=343$ nm)

EXAMPLE 14

42.8 mg of nonafluoropentanoic acid (Aldrich Co.) and 1 mg of Taxol were mixed in 50 μl of ethanol containing sodium hydroxide ($2.84 \times 10^{-4}$ mole). This mixture was added to 1 ml of the complex between the polyethylene glycol-polyethyleneimine copolymer and oleic acid sodium salt prepared as described in Example 10, above. After stirring overnight, the sample was centrifuged 10 minutes at 13000 RPM. 20 μl of supernatant was added to 1 ml of methanol and UV spectra were recorded. The Taxol concentration was calculated from the absorbency at 227 nm ($\epsilon=44,359$ ml/mg). The extinction coefficient was estimated in the presence of fluoroorganic component in methanol. The degree of Taxol solubilization was 74.4%. The size of the complex particles loaded with the Taxol/Fluoroorganic compound mixture determined by dynamic light scattering as described in Example 3, above, was 61 nm.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope of the appended claims.

What is claimed is:

1. A composition comprising a therapeutic or diagnostic agent and a supramolecular complex, said complex comprising as constituents
   (i) a block copolymer, having at least one nonionic, water soluble segment and at least one polyionic segment, and
   (ii) at least one charged surfactant having hydrophobic groups, the charge of said surfactant being opposite to the charge of the polyionic segment of said block copolymer, wherein the block copolymer constituent is not crosslinked to form networks, the constituents of said complex are bound by interaction between said opposite charges and between surfactant hydrophobic groups, and the ratio of net charge of said surfactant to the net charge of the polyanionic segment present in said block copolymer constituent of said complex is between about 0.01 and about 100.

2. A composition as claimed in claim 1, wherein the nonionic segment of said block copolymer is selected from the group consisting of polyetherglycols, copolymers of ethylene oxide and propylene oxide, polysaccharides, and homopolymers and copolymers of vinyl compounds selected from the group consisting of acrylamide, acrylic acid esters, methacrylamide, methacrylic esters, N-(2-hydroxypropyl)methacrylamide, vinyl alcohol, vinyl pyrrolidone, vinyl triazole, or the N-oxide of vinylpyridine and polyorthoester.

3. A composition as claimed in claim 1, wherein said polyanionic segment is selected from the group consisting of polymethacrylic acids and its salts, polyacrylic acid and its salts, copolymers of methacrylic acid and its salts, copolymers of acrylic acid and its salts, heparin, poly(phosphate), polymaleic acid, polylactic acid, nucleic acid or carboxylated dextran.

4. A composition as claimed in claim 1, wherein said polyanionic segment is a homopolymer or a co-polymer prepared from a monomer which polymerizes to form a product with carboxyl pendant groups, said monomer being selected from the group consisting of acrylic acid, aspartic acid (amino acid), 1,4-phenylenediacrylic acid citraconic acid, citraconic anhydride, trans cinnamic acid, 4-hydroxy-3-methoxy cinnamic acid, p-hydroxy cinnamic acid, trans-glutaconic acid, glutamic acid (amino acid), itaconic acid, linoleic acid, linolenic acid, methacrylic acid, maleic acid, maleic anhydride, mesaconic acid, trans-β-hydromuconic acid, trans-traumatic acid, vinyl benzoic acid, vinyl glycolic acid.

5. A composition as claimed in claim 1, wherein said surfactant is selected from the group consisting of lipophilic quaternary ammonium salts, lipopolyamines, lipophilic polyamino acids, lipophilic primary-, secondary-, tertiary- and heterocyclic amines, lipophilic imidazoles, lipophilic piperidinium salts, lipophilic quinaldinium salts, lipophilic azonium and azolium salts, pH-sensitive cationic lipids, dicationic bolaform electrolytes or a mixture of said surfactants.

6. A composition as claimed in claim 1, further including a nonionic surfactant.

7. A composition as claimed in claim 6, wherein said nonionic surfactant is selected from the group consisting of dioleoyl phosphatidylethanolamine, dioleoyl phosphatidylcholine, or a mixture of said nonionic surfactants.

8. A composition comprising a therapeutic or diagnostic agent and a composition of matter forming a supramolecular complex in aqueous medium and comprising as constituents (1) a block colpolymer, having at least one nonionic, water soluble segment and at least one polycationic segment, and (ii) at least one charge surfactant having hydrophobic groups, the charge of said surfactant being opposite to the charge of the polycationic segment of said block copolymer, the constituents of said complex being bound by interaction between said opposite charges and between surfactant hydrophobic groups, with the proviso that when said therapeutic or diagnostic agent is an ionic substance having a net charge opposite to the charge of said block copolymer, the net charge of said diagnostic or therapeutic agent is no more than 10, the ratio of the net charge of said surfactant to the net charge of the polycationic segment present in said block copolymer constituent of said complex is between about .01 and about 100, and said supramolecular complex has a particle sizeof less then 500 nm.

9. A composition as claimed in claim 8, wherein said polycationic segment is selected from the group consisting of polyamino acid, alkanolamine esters of polymethacrylic acid, polyamines, polyalkyleneimines, polyvinyl pyridine and quaternary ammonium salts of said polycationic segments.

10. A composition as claimed in claim 8, comprising an anionic surfactant selected from the group consisting of alkyl sulfates, alkyl sulfonates, fatty acid soaps, salts of hydrox-, hydroperoxy-, polyhydroxy-, epoxy- fatty acids, salts of mono- and polycarboxylic acids, prostanoic acid and prostaglandins, leukotrienes and lipoxines, alkyl phosphates, alkyl phosphonates, lipids, sodium-dialkyl sufosuccinate, n-alkyl ethoxylated sulfates, cholate and desoxycholate of bile salts, perfluorocarboxylic acids, fluoroaliphatic phosphonates, fluoroaliphatic suphates.

11. A composition as claimed in claim 1, in the form of vesicles, said vesicles having an internal volume containing said therapeutic or diagnostic agent.

12. A composition as claimed in claim 1, wherein said therapeutic or diagnostic agent is a charged species, having a positive or negative charge.

13. A composition as claimed in claim 1, wherein said therapeutic or diagnostic agent is a constituent of said supramolecular complex.

14. A composition as claimed in claim 1, wherein said therapeutic or diagnostic agent is selected from the group consisting of analgesic agents, anti-inflamatory agents, antibacterial agents, antiviral agents, antifungal agents, antiparasitic agents, tumoricidal or anti-cancer agents, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-glaucomic agents, mydriatic compounds and local anesthetics.

15. A composition as claimed in claim 1, wherein said charge ratio is between about 0.1 and 10.

16. A composition as claimed in claim 8, wherein said charge ratio is between about 0.1 and 10.

17. A composition as claimed in claim 8, wherein said supramolecular complex has a particle size less than 200 nm.

18. A composition as claimed in claim 8, wherein said supramolecular complex has a particle size less than 100 nm.

19. A composition as claimed in claim 8 in the form of vesicles said vesicles having an internal volume comprising said therapeutic or diagnostic agent.

20. A compositon as claimed in claim 8, wherein said therapeutic or diagnostic agent is a charged species, having a positive or negative charge.

21. A composition as claimed in claim 8, wherein said therapeutic or diagnostic agent is a constituent of said supramolecular complex.

22. A composition as claimed in claim 8, wherein said therapeutic or diagnostic agent is selected from the group consisting of analgesic agents, anti-inflammatory agents, antibacterial agents, antiviral agents antifungal agents, antiparasitic agents, tumoricidal or anti-cancer agents, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-glaucomic agents, mydriatic compounds, and local anesthetics.

23. The composition of claim 4, where said copolymer also comprises at least one monomer selected from the group consisting of 2-propene-1-sulfonic acid, 4-styrene sulfonic acid, vinylsulfonic acid and vinyl phosphate acid.

* * * * *